United States Patent [19]

Buchecker et al.

[11] Patent Number: 5,284,956
[45] Date of Patent: Feb. 8, 1994

[54] LIQUID CRYSTALLINE MIXTURES CONTAINING 2-(2-FLUOROPHENYL) PYRIDINES

[75] Inventors: Richard Buchecker, Zurich, Switzerland; Assya I. Pavluchenko; Vladimir F. Petrov, both of Moscow, U.S.S.R.; Martin Schadt, Selitsberg, Switzerland; Natalia I. Smirnova, Dolgoprudny, Moscow Region; Victor V. Titov, Moscow, both of U.S.S.R.

[73] Assignees: Hoffmann-La Roche Inc., Nutley, N.J.; Niopic Moscow Research and Production Association

[21] Appl. No.: 857,702

[22] Filed: Mar. 25, 1992

Related U.S. Application Data

[63] Continuation of Ser. No. 400,595, Aug. 29, 1989, abandoned.

[30] Foreign Application Priority Data

Sep. 6, 1988 [CH] Switzerland .............. 3334/88

[51] Int. Cl.⁵ .................. C07D 213/26; C07D 213/30
[52] U.S. Cl. ...................................... 546/339; 546/346
[58] Field of Search .......................... 546/339, 346

[56] References Cited

U.S. PATENT DOCUMENTS

| | | | |
|---|---|---|---|
| 4,684,220 | 8/1987 | Shionozaki et al. | 546/339 X |
| 4,765,924 | 8/1988 | Inoue et al. | 546/339 X |
| 4,772,416 | 9/1988 | Goto et al. | 252/299.61 |
| 4,781,857 | 11/1988 | Inoue et al. | 546/339 X |
| 4,795,587 | 1/1989 | Ohno et al. | 546/339 X |
| 4,820,839 | 4/1989 | Krause et al. | 544/316 |

FOREIGN PATENT DOCUMENTS

| | | |
|---|---|---|
| 233706 | 2/1987 | European Pat. Off. . |
| 239403 | 3/1987 | European Pat. Off. . |
| 240320 | 3/1987 | European Pat. Off. . |
| 244939 | 3/1987 | European Pat. Off. . |
| 3524489 | 7/1985 | Fed. Rep. of Germany . |
| 86/07085 | 12/1986 | World Int. Prop. O. . |

OTHER PUBLICATIONS

A. I. Pavluchenko, V. V. Titov, and N. I. Smirnova, *Advances in Liquid Crystal Research and Applications*, p. 1007, 1980.

Primary Examiner—Mary C. Lee
Assistant Examiner—Jacqueline Haley
Attorney, Agent, or Firm—George M. Gould; George W. Johnston

[57] ABSTRACT

Compounds of the formula

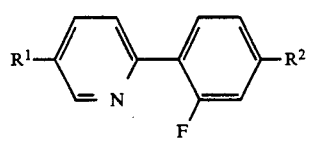

I wherein
$R^1$ is alkyl or trans-4-alkylcyclohexyl and
$R^2$ is alkyl, alkoxy or trans-4-alkylcyclohexyl their preparation, liquid crystalline mixtures containing these compounds and their use for electro-optical purposes.

5 Claims, No Drawings

LIQUID CRYSTALLINE MIXTURES CONTAINING 2-(2-FLUOROPHENYL) PYRIDINES

This application is a continuation of application Ser. No. 07/400,595, filed Aug. 29, 1989 now abandoned.

FIELD OF THE INVENTION

The present invention is concerned with novel 2-(2-fluorophenyl)pyridines, their preparation, liquid crystalline mixtures which contain these compounds and their use for electro-optical purposes.

BACKGROUND OF THE INVENTION

Liquid crystals are used primarily as dielectrics in indicating devices, since the optical properties of such substances can be influenced by an applied voltage. Electro-optical devices based on liquid crystals are well-known to the person skilled in the art and can be based on various effects. Such devices are, for example, cells having dynamic scattering. DAP cells (deformation of aligned phases). guest/host cells. TN cells having a twisted nematic structure. STN cells ("super-twisted nematic"). SBE cells ("super-birefringence effect") and OMI cells ("optical mode interference"). The most common indicating devices are based on the Schadt-Helfrich effect and have a twisted nematic structure.

The liquid crystal materials must have a good chemical and thermal stability and a good stability towards electric fields and electromagnetic radiation. Further, the liquid crystal materials should have a low viscosity and in the cells should give short response times, low threshold potentials and a high contrast. Furthermore, at usual operating temperatures, that is, in a range below and above room temperature which is as broad as possible, they should have a suitable mesophase, for example a nematic or cholesteric mesophase for the cells referred to above. In addition, there has also recently been an increased interest in the especially rapidly switching ferroelectric liquid crystals having a chiral tilted, smectic mesophase, especially a smectic C phase.

Since liquid crystals are generally used as mixtures of several components, it is important that the components have a good miscibility with one another. Other properties such as the electrical conductivity, the dielectric anisotropy and the optical anisotropy must fulfil different requirements depending on the type of cell and field of application. For example, materials for cells having a twisted nematic structure should have a positive dielectric anisotropy and an electrical conductivity which is as small as possible.

SUMMARY OF THE INVENTION

The present invention concerns compounds of formula

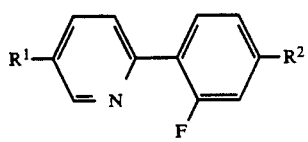

wherein $R^1$ is alkyl or trans-4-alkylcyclohexyl; and $R^2$ is alkyl, alkoxy or trans-4-alkylcyclohexyl.

DETAILED DESCRIPTION OF THE INVENTION

The present invention provides the compounds of the formula

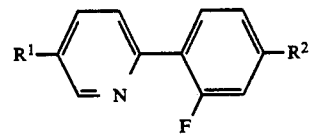

wherein $R^1$ is alkyl or trans-4-alkylcyclohexyl and $R^2$ is alkyl, alkoxy or trans-4-alkylcyclohexyl.

The compounds in accordance with the invention are useful in liquid crystalline mixtures because they have a very high chemical and thermal stability and a high stability towards electric fields and electromagnetic radiation. They have a comparatively low viscosity, they have only a small absolute value of the dielectric anisotropy, they have a good miscibility with known liquid crystal materials and, when used in liquid crystal mixtures, they make possible low operating and threshold potentials and a high multiplexibility.

In contrast to known, non-polar liquid crystal components having a nitrogen heterocycle, in the case of the compounds in accordance with the invention highly ordered smectic phases are for the most part completely suppressed and, in spite of this, comparatively broad mesophase ranges are obtained. The compounds in accordance with the invention therefore have, especially when the alkyl and alkoxy residues are not too long (the sum of the carbon atoms in the two alkyl residues in $R^1$ and $R^2$ or the sum of the carbon atoms in the alkyl residue in $R^1$ and in the alkoxy residue in R is a maximum of about 12), mainly a pure nematic phase or, in the case of the optically active compounds, a cholesteric phase. They are therefore suitable primarily as non-polar components for nematic and cholesteric liquid crystal mixtures. Further, the compounds in accordance with the invention are well suited as components for ferroelectric mixtures, in which case the alkyl and alkoxy residues are advantageously somewhat longer. Preferably, the sum of the carbon atoms in the alkyl residues in $R^1$ and $R^2$ or the sum of the carbon atoms in the alkyl residue in $R^1$ and in the alkoxy residue in $R^2$ is at least about 8, for example about 10-18.

The optically active compounds of formula I induce a comparatively strong twisting, that is, a small pitch, in liquid crystal mixtures. Further, they are suitable for inducing a spontaneous polarization in ferroelectric mixtures. The induced twisting and the induced spontaneous polarization are generally especially great when $R^1$ is alkyl and $R^2$ is alkyl or alkoxy and/or the center of chirality is close to the neighboring ring.

The compounds of formula I in which $R^1$ is alkyl and $R^2$ is alkyl or alkoxy are especially suitable as low-viscosity doping substances. The compounds of formula I in which $R^1$ and/or $R^2$ are trans-4-alkylcyclohexyl have high clearing points and are suitable, inter alia, for increasing the clearing points of mixtures.

The above term "alkyl" and the alkyl residue in "trans-4-alkylcyclohexyl" and in "alkoxy" embrace in each case straight-chain and branched residues which preferably have 1-18 carbon atoms. Residues having 1-12, especially 1-7, carbon atoms are especially preferred; for ferro-electric applications the residues can, however, advantageously also be longer and preferably have about 6-14, particularly about 6-12, carbon atoms. Straight-chain residues are generally preferred. If desired, however, one or both residues can be branched and, if desired, can be chiral. In the case of branched groups, the term "alkyl" or the alkyl residue in "trans-4-alkylcyclohexyl" and "alkoxy" preferably stands for 1-methylalkyl (=2-alkyl), 2-methylalkyl or isoalkyl.

In accordance with the above, $R^1$ preferably is $C_1-C_{18}$-alkyl or trans-4-($C_1-C_{18}$-alkyl)cyclohexyl, particularly $C_1-C_{12}$-alkyl or trans-4-($C_1-C_{12}$-alkyl)cyclohexyl, especially $C_1-C_7$-alkyl, or trans-4-($C_1-C_7$-alkyl)cyclohexyl. Preferably, the alkyl residue in R is always straight-chain. $R^2$ preferably is $C_1-C_{18}$-alkyl. $C_1-C_{18}$-alkoxy or trans-4-($C_1-C_{18}$-alkyl)cyclohexyl, particularly $C_1-C_7$-alkoxy or trans-4-($C_1-C_7$-alkyl)-cyclohexyl. The alkyl residue in $R^2$ is preferably straight-chain when $R^2$ signifies alkyl or trans-4-alkylcyclohexyl. An alkoxy group $R^2$ can be straight-chain or branched. 1-Methylalkoxy (=2-alkoxy) and 2-methylalkoxy are preferred branched alkoxy groups.

Examples of preferred alkyl groups are methyl, ethyl, propyl, butyl, s-butyl, pentyl (=1-pentyl). 2-pentyl (=1-methylbutyl), 2-methylbutyl, isopentyl, hexyl (=1-hexyl), 2-hexyl (=1-methylpentyl), 3-methylpentyl, heptyl, octyl (=1-octyl), 2-octyl (=1-methylheptyl), nonyl, decyl, undecyl and dodecyl. Examples of preferred alkoxy groups are methoxy, ethoxy, propyloxy, butyloxy, s-butyloxy, pentyloxy (=1-pentyloxy), 2-pentyloxy (=1-methylbutyloxy), 2-methylbutyloxy, hexyloxy (=1-hexyloxy), 2-hexyloxy (=1-methylpentyloxy), 3-methylpentyloxy, heptyloxy, octyloxy (=1-octyloxy), 2-octyloxy (=1-methylheptyloxy), nonyloxy, decyloxy, undecyloxy and dodecyloxy. Examples of preferred trans-4alkylcyclohexyl groups are those in which "alkyl" stands for methyl, ethyl, propyl, butyl, s-butyl, pentyl, 2-methylbutyl, hexyl, 3-methylpentyl, heptyl or octyl. The chiral groups can be present in the R- or S-form.

A preferred group of compounds in accordance with the invention comprises those in which $R^2$ denotes a straight-chain or a branched, optionally chiral, alkoxy group. In this case, R preferably is n-alkyl or trans-4-n-alkylcyclohexyl.

The compounds of formula I can be prepared in accordance with the invention by reacting a compound of the formula

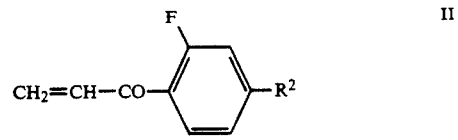

wherein $R^2$ has the above significance, with a piperidine derivative of the formula

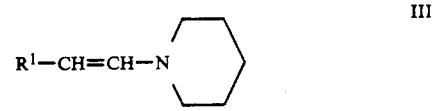

wherein $R^1$ has the above significance, and subsequently with hydroxylamine in the presence of acid.

The reaction can be effected in a manner known per se and under usual conditions, for example according to the method described in the detailed Examples.

The starting materials of formula III are known or are analogues of known compounds. The preparation of the starting materials of formulas II and III and their reaction to give compounds of formula I is illustrated on the basis of Schemes 1 and 2 in which $R^3$ is alkyl and $R^4$ is hydrogen or alkyl and $R^1$ and $R^2$ have the above significances:

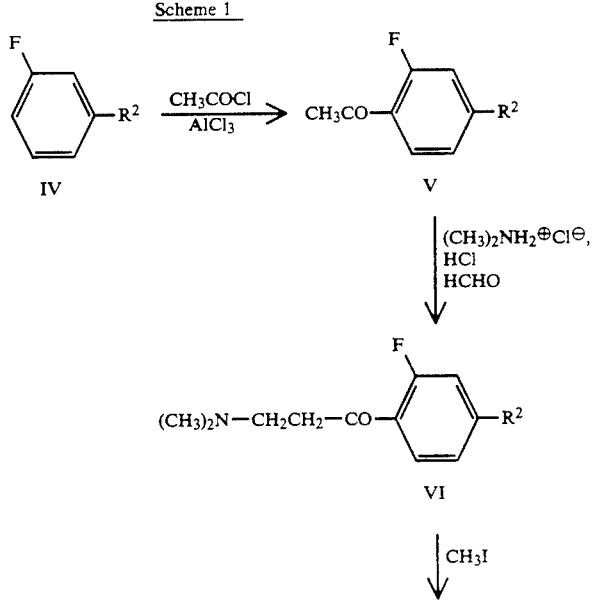

5,284,956
-continued
Scheme 1
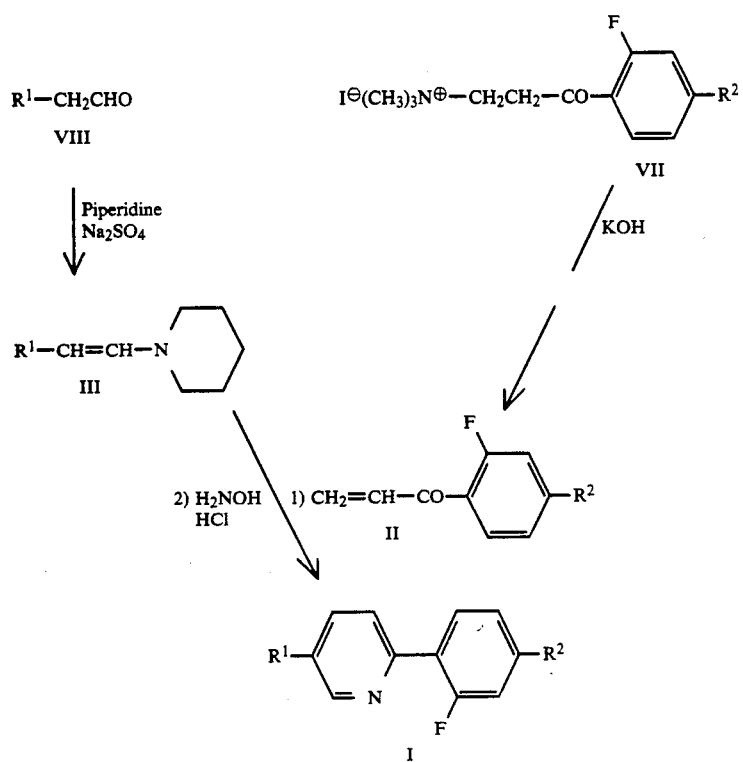
Scheme 2
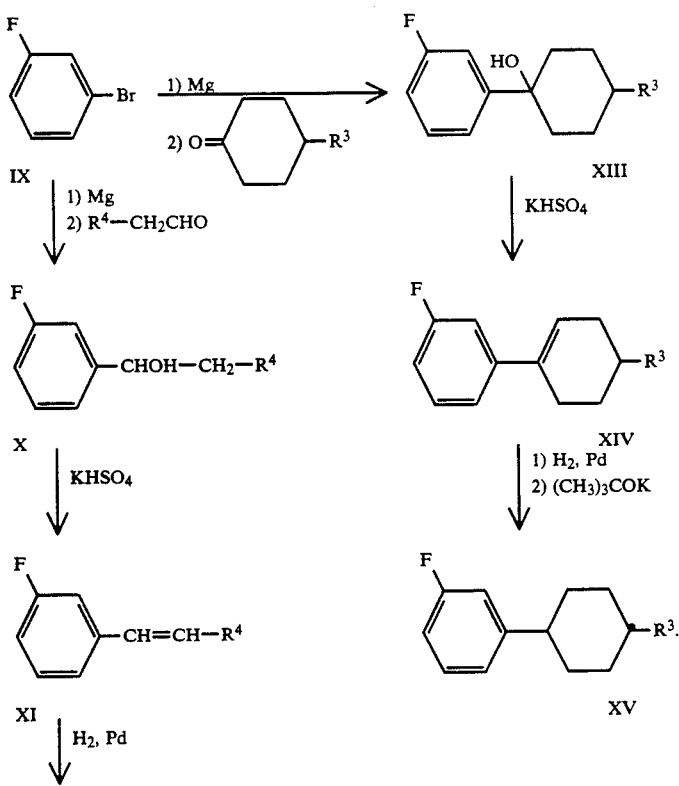

Scheme 2

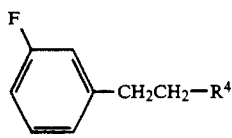

XII

The starting materials of formula VIII are known or are analogues of known compounds. The starting materials of formula IV in which $R^2$ is methyl or methoxy are known and are commercially available. The compounds of formula IV in which $R^2$ is alkoxy can be obtained from the known m-fluorophenol according to usual methods, for example by etherification with an alkyl bromide in the presence of sodium carbonate. The preparation of the compounds of formula IV in which $R^2$ is alkyl or trans-4-alkylcyclohexyl can be effected according to the method illustrated in Scheme 2. If desired, instead of being reacted with the aldehyde of the formula $R^4$—$CH_2CHO$. the compound of formula IX can also be reacted with a ketone or with an aldehyde which has a chain-branching in the α-position.

The compounds of formula I can be used in the form of mixtures with one another and/or with other liquid crystal components such as for example, with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, phenylcyclohexanes, cyclohexylcyclohexanes, phenylpyrimidines, cyclohexylpyrimidines, phenyldioxanes, 2-cyclohexyl-1-phenylethanes, terphenyls, cyclohexylbiphenyls, cyclohexylphenylpyrimidines and the like. Such substances are known to the person skilled in the art and many of them are, moreover, commercially available.

The liquid crystalline mixtures in accordance with the invention contain at least two components, of which at least one component is a compound of formula I. A second component and optionally further components can be further compounds of formula I and/or other liquid crystal components.

The compounds of formula I are especially suitable for nematic mixtures or, insofar as at least one component of the mixture is optically active, also for cholesteric mixtures. A preferred field of application is the use as dielectrics in liquid crystal indicating devices having a twisted nematic liquid crystal structure such as TN cells, STN cells, SBE cells and OMI cells. Preferred mixtures are therefore those which contain one or more compounds of formula I and one or more compounds having positive dielectric anisotropy. Further, the compounds of formula I are suitable as components of chiral tilted smectic phases.

The amount of compounds of formula I in the mixtures in accordance with the invention can vary over a relatively wide range and, for example, can amount to about 1-60 wt. %. An amount of about 3-30 wt.%, especially about 5-20 wt. %, of compounds of formula I is generally preferred.

The nematic or cholesteric mixtures in accordance with the invention preferably contain, in addition to one or more compounds of formula I, one or more compounds from the group of compounds of the formulas

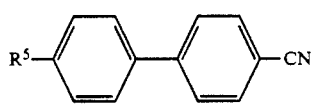

XVI

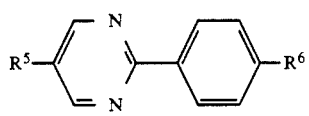

XVII

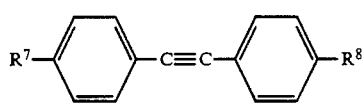

XVIII

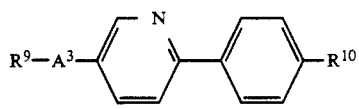

XIX

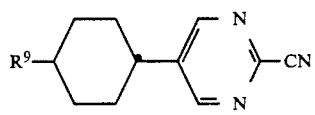

XX

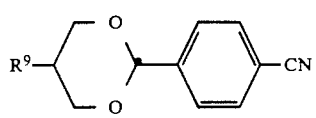

XXI

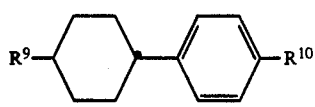 XXII

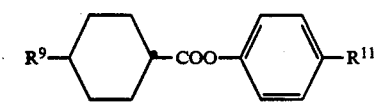 XXIII

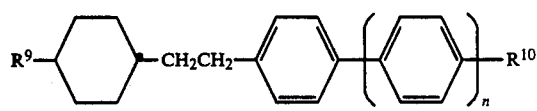 XXIV

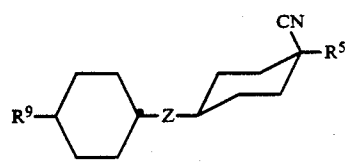 XXV

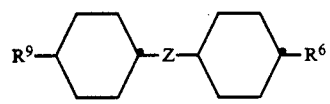 XXVI

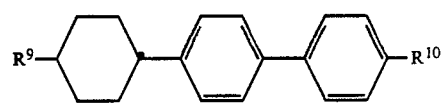 XXVII

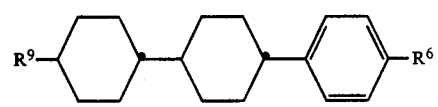 XXVIII

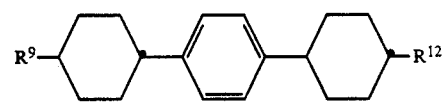 XXIX

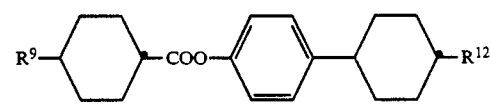 XXX

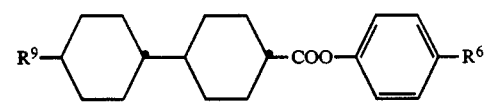 XXXI

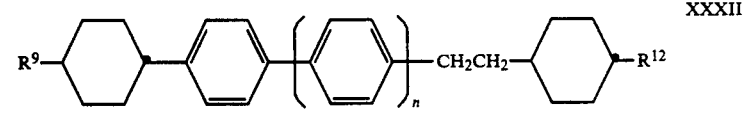 XXXII

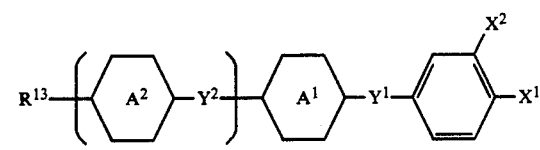 XXXIII wherein $R^5$ is alkyl, 3E-alkenyl or 4-alkenyl; $R^6$ represents cyano, alkyl, 1E-alkenyl, 3E-alkenyl, 4-alkenyl, alkoxy, 2E-alkenyloxy or 3-alkenyloxy; $R^7$ and $R^8$ denote alkyl or alkoxy; $R^9$ and $R^{12}$ each independently are alkyl, 1E-alkenyl, 3E-alkenyl or 4-alkenyl; $A^3$ represents a single covalent bond, 1,4-phenylene or trans-1,4-cyclohexylene; $R^{10}$ denotes cyano, —NCS, alkyl, 1E-alkenyl, 3E-alkenyl, 4-alkenyl, alkoxy, 2E-alkenyloxy or 3-alkenyloxy; $R^{11}$ is alkoxy, 2E-alkenyloxy or 3-alkenyloxy; n stands for the number 0 or 1; Z represents a single covalent bond or —CH$_2$CH$_2$—; $X^1$ denotes fluorine or chlorine and $X^2$ is hydrogen, fluorine or chlorine; $R^{13}$ is alkyl, 3E-alkenyl, 4-alkenyl, alkoxy, 2E-alkenyloxy or 3-alkenyloxy; one of the groups $Y^1$ and $Y^2$ is a single covalent bond, —COO—, —OOC—, —CH$_2$CH$_2$—, —CH$_2$O— or —OCH$_2$— and the other of the groups $Y^1$ and $Y^2$ is a single covalent bond; and rings $A^1$ and $A^2$ each independently are substituted or unsubstituted trans-1,4-cyclohexylene, in which optionally 2 non-adjacent CH$_2$ groups are replaced by oxygen, or substituted or unsubstituted 1,4-phenylene, in which optionally 1 CH group or 2 CH groups is/are replaced by nitrogen.

The term "substituted or unsubstituted trans-1,4-cyclohexylene, in which optionally 2 non-adjacent CH$_2$ groups are replaced by oxygen" embraces especially trans-1,4-cyclohexylene and trans-m-dioxane-2,5-diyl as well as rings which are substituted with substituents which are usual in liquid crystals such as cyano, methyl, fluorine or chlorine, for example 1-cyano-trans-1,4-cyclohexylene or 2-methyl-trans-1,4-cyclohexylene.

The term "substituted or unsubstituted 1,4-phenylene, in which optionally 1 CH group or 2 CH groups is/are replaced by nitrogen" embraces especially 1,4-phenylene, pyridine-2,5-diyl, pyrazine-2,5-diyl and pyrimidine-2,5-diyl as well as rings which are substituted with substituents which are usual in liquid crystals such as cyano, methyl, fluorine or chlorine, for example 2-cyano-1,4-phenylene, 2-fluoro-1,4-phenylene, 2-chloro-1,4-phenylene or 2-methyl-1,4-phenylene.

The cyano and halo compounds of formulas XVI, XVII, XIX, XX, XXI, XXII, XXIV, XXVI, XXVII, XXVIII, XXXI and XXXIII are preferred mixture components having a positive dielectric anisotropy. Preferably, nematic and cholesteric mixtures having a positive dielectric anisotropy contain about 20–70 wt. %, especially about 25–50 wt. %, of one or more of these compounds.

The mixtures in accordance with the invention can also contain optically active compounds (for example, optically active 4'-alkyl- or 4'-alkoxy-4-biphenylcarbonitriles) and/or dichroic coloring substances (for example, azo, azoxy or anthra- quinone coloring substances). The amount of such compounds is determined by the solubility, the desired pitch, color, extinction and the like. In general, the amount of optically active compounds and dichroic coloring substances in the final mixture amounts to a maximum of in each case about 10 wt. %.

The mixtures in accordance with the invention for smectic applications (especially for tilted smectic or chiral tilted smectic phases) preferably contain, in addition to one or more compounds of formula I, one or more compounds from the group of compounds of the formulas

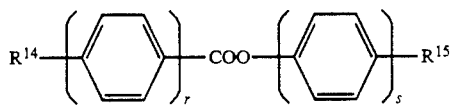

XXXIV

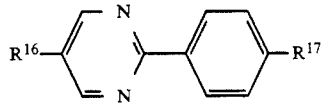

XXXV

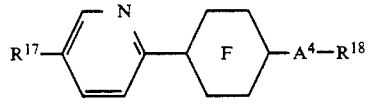

XXXVI

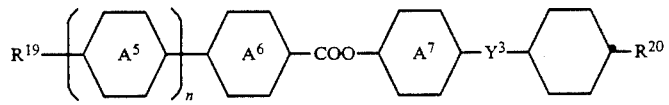

XXXVII

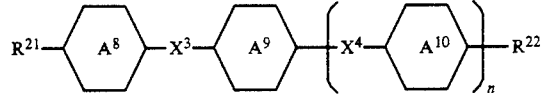

XXXVIII

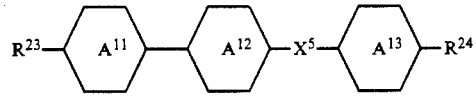

XXXIX

XL wherein $R^{14}$ and $R^{15}$ are alkyl, alkoxy, alkanoyl, alkanoyloxy, alkoxycarbonyl or alkoxycarbonyloxy with up to 18 carbon atoms; r and s each individually are 1 or 2; $R^{16}$ and $R^{17}$ represent alkyl or alkoxy with 1–18 carbon atoms; $A^4$ is a single covalent bond, trans-1,4-cyclohexylene or 1,4-phenylene which is optionally substituted with halogen or methyl; ring F represents trans-1,4-cyclohexylene or 1,4-phenylene which is optionally substituted with halogen or methyl; $R^{17}$ and $R^{18}$ each denote an optionally halogen-substituted alkyl or alkenyl group in which optionally one $CH_2$ group or two non-adjacent $CH_2$ groups is/are replaced by —O—, —COO— and/or —OOC—; n stands for the number 0 or 1; $Y^3$ is a single covalent bond, —CH—CH$_2$—, —OCH$_2$—, —COO— or —OOC—; rings $A^5$, $A^6$ and $A^7$ denote 1,4-phenylene which is optionally substituted with cyano, halogen or lower alkyl; $R^{19}$ and $R^{20}$ each individually represent optionally halogen-substituted $C_1$-$C_{18}$-alkyl or optionally halogen-substituted $C_2$-$C_{18}$-alkenyl in which optionally one $CH_2$ group or two non-adjacent $CH_2$ groups is/are replaced by oxygen; $X^3$ represents a single covalent bond, —COO— or —OOC— and $X^4$ represents a single covalent bond, —COO—, —OOC—, —CH$_2$CH$_2$—, —OCH$_2$— or —CH$_2$O—; rings $A^8$, $A^9$ and $A^{10}$ each independently are unsubstituted or cyano-, halogen- or lower alkyl-substituted 1,4-phenylene or one of the rings also is pyrimidine-2,5-diyl or pyrazine-2,5-diyl and/or, when n stands for the number 1, one of the rings also is trans-1,4-cyclohexylene or trans-m-dioxane-2,5-diyl; $R^{21}$ is an optionally halogen-substituted alkenyl group with up to 18 carbon atoms in which optionally 1 $CH_2$ group or 2 non-adjacent $CH_2$ groups is/are replaced by —O—, —CO—, —COO— or —OOC—; $R^{22}$ is an optionally halogen-substituted alkyl group with up to 18 carbon atoms in which optionally 1 $CH_2$ group or 2 non-adjacent $CH_2$ groups is/are replaced by —O—, —CO—, —COO— or —OOC— and/or optionally a C—C single bond is replaced by a C—C double bond; $X^5$ denotes a single covalent bond, —COO—, —OOC—, —CH$_2$CH$_2$—, —OCH$_2$— or —CH$_2$O—; one of rings $A^{11}$, $A^{12}$ and $A^{13}$ represents pyrimidine-2,5-diyl, one of rings $A^{11}$, $A^{12}$ and $A^{13}$ is unsubstituted or cyano-, halogen- or lower alkyl-substituted 1,4-phenylene and one of rings $A^{11}$, $A^{12}$ and $A^{13}$ represents trans-1,4-cyclohexylene or unsubstituted or cyano-, halogen- or lower alkyl-substituted 1,4-phenylene; and $R^{23}$ and $R^{24}$ each independently are an optionally halogen-substituted alkyl group with up to 18 carbon atoms in which optionally 1 $CH_2$ group or 2 non-adjacent $CH_2$ groups is/are replaced by —O—, —CO—, —COO— and/or —OOC—; $X^6$ denotes a single covalent bond, —COO—, —OOC—, —CH$_2$CH$_2$—, —OCH$_2$— or —CH$_2$O—; one of rings $A^{14}$, $A^{15}$ and $A^{16}$ represents trans-m-dioxane-2,5-diyl and the other two of rings $A^{14}$, $A^{15}$ and $A^{16}$ each independently represent unsubstituted or cyano-, halogen- or lower alkyl-substituted 1,4-phenylene; $R^{25}$ and $R^{26}$ each independently are an optionally halogen-substituted alkyl group with up to 18 carbon atoms in which optionally 1 $CH_2$ group or 2 non-adjacent $CH_2$ groups is/are replaced by —O—, —CO—, —COO— and/or —OOC—.

The preparation of the mixtures in accordance with the invention and the preparation of electro-optical devices can be effected in a manner known per se.

The preparation of the compounds of formula I and liquid crystalline mixtures containing these compounds are illustrated in more detail by the following Examples. C is a crystalline phase, S is a smectic phase, $S_C$ is a smectic C phase, N is a nematic phase. Ch is a cholesteric phase and I is the isotropic phase. $V_{10}$ denotes the voltage for 10% transmission (direction of view perpendicular to the plate surface). $\Delta\epsilon = \epsilon - \epsilon$ denotes the dielectric anisotropy, whereby $\epsilon$ is the dielectric constant parallel to the longitudinal axis of the molecule and $\epsilon$ is the dielectric constant perpendicular thereto. $\Delta n$ denotes the optical anisotropy.

The following Examples illustrate the present invention but are not intended to limit its extent in any manner.

Unless otherwise stated, percentages and ratios relating to solvent mixtures are expressed in volume, purity data determined by gas chromatography are expressed in area %, and the remaining percentages and ratios are expressed in weight. Temperatures are in degrees Celsuis (°C.), normal pressure is about 1 atmosphere, and room temperature is about 23° C. Examples were carried out as written unless otherwise indicated.

EXAMPLE 1

0.078 mol of anhydrous sodium sulfate and 0.086 mol of piperidine were mixed and treated dropwise at −5° C. under nitrogen with 0.039 mol of trans-4-propylcyclohexylacetaldehyde. The reaction mixture was stirred at room temperature for 24 hours. Subsequently the precipitate was filtered off and washed with hexane. Distillation of the combined filtrates under a vacuum gave 1-[2-(trans-4-propylcyclohexyl)vinyl]piperidine of b.p. 118°–120° C./1 Torr in 75% yield.

The following compounds can be prepared in an analogous manner:

1-[2-(trans-4-Methylcyclohexyl)vinyl]piperidine;
1-[2-(trans-4-ethylcyclohexyl)vinyl]piperidine, b.p. 110°–113° C./1 Torr;
1-[2-(trans-4-butylcyclohexyl)vinyl]piperidine;
1-[2-(trans-4-pentylcyclohexyl)vinyl]piperidine b.p. 153°–155° C./1 Torr;
1-[2-(trans-4-hexylcyclohexyl)vinyl]piperidine;
1-[2-(trans-4-heptylcyclohexyl)vinyl]piperidine;
1-[2-(trans-4-octylcyclohexyl)vinyl]piperidine;
1-(1-propenyl)piperidine;
1-(1-butenyl)piperidine;
1-(1-pentenyl)piperidine;
1-(1-hexenyl)piperidine;
1-(1-heptenyl)piperidine;
1-(1-octenyl)piperidine;
1-(1-nonenyl)piperidine;
1-(1-decenyl)piperidine;
1-(1-undecenyl)piperidine;
1-(1-dodecenyl)piperidine.

EXAMPLE 2 a) A mixture of 0.13 mol of 1-acetyl-2-fluoro-4-methoxybenzene (preparable by etherifying m-fluorophenol with methyl bromide in the presence of sodium carbonate and subsequently acetylating the 3-fluoro-1-methoxybenzene with acetyl chloride in the presence of aluminium trichloride), 0.13 mol of dimethylamine hydrochloride, paraformaldehyde (0.22 mol based on formaldehyde content), 25 ml of anhydrous isopropyl alcohol and 0.02 ml of concentrated hydrochloric acid was boiled for 8 hours. Subsequently, the reaction mixture was cooled, diluted with 100 ml of anhydrous acetone and filtered. The residue of 1-[3-(dimethylamino)-propionyl]-2-fluoro-4-methoxybenzene hydrochloride was dissolved in 200 ml of water. The solution was adjusted to pH 8 with 5 percent (wt./vol.) sodium hydroxide solution and extracted with methylene chloride. The organic phase was dried with anhydrous sodium sulfate and filtered.

b) The obtained solution of 1-[3-(dimethylamino)propionyl]-2-fluoro-4-methoxybenzene was treated with 0.15 mol of methyl iodide while stirring at 10°-15° C. and the mixture was stored in the dark for 24 hours. Subsequently, the solid 1-[3-(dimethylamino)propionyl]-2-fluoro-4-methoxybenzene iodomethylate was filtered off and washed with methylene chloride.

c) The 1-[3-(dimethylamino)propionyl]-2-fluoro-4-methoxybenzene iodomethylate obtained was suspended in 220 ml of water and 360 ml of methylene chloride. The suspension was treated with a solution of 6.4 g of potassium hydroxide in 60 ml of water within 15 minutes while stirring intensively, whereby the solid iodomethylate disappeared within 15-20 minutes. The organic phase was separated and the aqueous phase was extracted twice with 50 ml of methylene chloride each time. The combined organic extracts were washed neutral with water, dried over anhydrous sodium sulfate, filtered and treated with a small amount of hydroquinone for stabilization purposes. After separation of the solvent in a vacuum the resulting unstable 1-acrylyl-2-fluoro-4-methoxybenzene was used directly in the next step (Example 3) without further purification.

The following compounds can be prepared in an analogous manner:
1-Acrylyl-2-fluoro-4-ethoxybenzene;
1-acrylyl-2-fluoro-4-propyloxybenzene;
1-acrylyl-2-fluoro-4-butyloxybenzene;
1-acrylyl-2-fluoro-4-pentyloxybenzene;
1-acrylyl-2-fluoro-4-hexyloxybenzene;
1-acrylyl-2-fluoro-4-(2S-hexyloxy)benzene;
1-acrylyl-2-fluoro-4-heptyloxybenzene;
1-acrylyl-2-fluoro-4-octyloxybenzene;
1-acrylyl-2-fluoro-4-(2S-octyloxy)benzene;
1-acrylyl-2-fluoro-4-nonyloxybenzene;
1-acrylyl-2-fluoro-4-methylbenzene;
1-acrylyl-2-fluoro-4-ethylbenzene;
1-acrylyl-2-fluoro-4-propylbenzene;
1-acrylyl-2-fluoro-4-butylbenzene;
1-acrylyl-2-fluoro-4-pentylbenzene;
1-acrylyl-2-fluoro-4-hexylbenzene;
1-acrylyl-2-fluoro-4-heptylbenzene;
1-acrylyl-2-fluoro-4-(trans-4-methylcyclohexyl)benzene;
1-acrylyl-2-fluoro-4-(trans-4-ethylcyclohexyl)benzene;
1-acrylyl-2-fluoro-4-(trans-4-propylcyclohexyl)benzene;
1-acrylyl-2-fluoro-4-(trans-4-butylcyclohexyl)benzene;
1-acrylyl-2-fluoro-4-(trans-4-pentylcyclohexyl)benzene;
1-acrylyl-2-fluoro-4-(trans-4-hexylcyclohexyl)benzene;
1-acrylyl-2-fluoro-4-(trans-4-heptylcyclohexyl)benzene.

EXAMPLE 3

0.03 mol of 1-acrylyl-2-fluoro-4-methoxybenzene was mixed at 0° C. with 0.03 mol of 1-[2-(trans-4-propylcyclohexyl)vinyl]piperidine and held at room temperature for 2 hours. The mixture was then treated with 90 ml of ethanol, 10 ml of water, 0.14 mol of hydroxylamine hydrochloride and 1 ml of concentrated hydrochloric acid and heated to reflux for 8 hours. Subsequently, about ⅔ of the solvent were removed by distillation. The concentrated mixture was diluted with 150 ml of water and adjusted to pH 8 with aqueous sodium carbonate solution. The organic layer was extracted with benzene. The extract was washed neutral with water, dried over sodium sulfate, filtered and concentrated. Chromatographic purification of the resulting residue on silica gel with benzene/hexane (vol. 1:1) gave 2-(4-methoxy-2-fluorophenyl)-5-(trans-4-propylcyclohexyl)pyridine in 20% yield; m.p. (C-N) 56.3° C., cl.p. (N-I) 180.6° C.

The following compounds can be prepared in analogous manner:
2-(4-Methoxy-2-fluorophenyl)-5-methylpyridine;
2-(4-methoxy-2-fluorophenyl)-5-ethylpyridine;
2-(4-methoxy-2-fluorophenyl)-5-propylpyridine;
2-(4-methoxy-2-fluorophenyl)-5-butylpyridine;
2-(4-methoxy-2-fluorophenyl)-5-pentylpyridine, m.p. 23.3° C.;
2-(4-methoxy-2-fluorophenyl)-5-hexylpyridine;
2-(4-methoxy-2-fluorophenyl)-5-heptylpyridine;
2-(4-ethoxy-2-fluorophenyl)-5-methylpyridine;
2-(4-ethoxy-2-fluorophenyl)-5-ethylpyridine;
2-(4-ethoxy-2-fluorophenyl)-5-propylpyridine;
2-(4-ethoxy-2-fluorophenyl)-5-butylpyridine;
2-(4-ethoxy-2-fluorophenyl)-5-pentylpyridine;
2-(4-ethoxy-2-fluorophenyl)-5-hexylpyridine;
2-(4-ethoxy-2-fluorophenyl)-5-heptylpyridine;
2-(4-propyloxy-2-fluorophenyl)-5-methylpyridine;
2-(4-propyloxy-2-fluorophenyl)-5-ethylpyridine;
2-(4-propyloxy-2-fluorophenyl)-5-propylpyridine;
2-(4-propyloxy-2-fluorophenyl)-5-butylpyridine;
2-(4-propyloxy-2-fluorophenyl)-5-pentylpyridine;
2-(4-propyloxy-2-fluorophenyl)-5-hexylpyridine;
2-(4-butyloxy-2-fluorophenyl)-5-methylpyridine;
2-(4-butyloxy-2-fluorophenyl)-5-ethylpyridine;
2-(4-butyloxy-2-fluorophenyl)-5-propylpyridine;
2-(4-butyloxy-2-fluorophenyl)-5-butylpyridine;
2-(4-butyloxy-2-fluorophenyl)-5-pentylpyridine;
2-(4-butyloxy-2-fluorophenyl)-5-hexylpyridine;
2-(4-pentyloxy-2-fluorophenyl)-5-methylpyridine;
2-(4-pentyloxy-2-fluorophenyl)-5-ethylpyridine;
2-(4-pentyloxy-2-fluorophenyl)-5-propylpyridine;
2-(4-pentyloxy-2-fluorophenyl)-5-butylpyridine;
2-(4-pentyloxy-2-fluorophenyl)-5-pentylpyridine;
2-(4-pentyloxy-2-fluorophenyl)-5-hexylpyridine;
2-(4-hexyloxy-2-fluorophenyl)-5-methylpyridine;
2-(4-hexyloxy-2-fluorophenyl)-5-ethylpyridine;
2-(4-hexyloxy-2-fluorophenyl)-5-propylpyridine;
2-(4-hexyloxy-2-fluorophenyl)-5-butylpyridine;
2-(4-hexyloxy-2-fluorophenyl)-5-pentylpyridine;
2-(4-hexyloxy-2-fluorophenyl)-5-hexylpyridine, m.p. (C-N) 16° C., cl.p. (N-I) 21.5° C.;
2-(4-hexyloxy-2-fluorophenyl)-5-heptylpyridine;
2-(4-hexyloxy-2-fluorophenyl)-5-octylpyridine;
2-(4-hexyloxy-2-fluorophenyl)-5-nonylpyridine;
2-(4-hexyloxy-2-fluorophenyl)-5-decylpyridine;
2-[4-(2S-hexyloxy)-2-fluorophenyl]-5-methylpyridine;
2-[4-(2S-hexyloxy)-2-fluorophenyl]-5-ethylpyridine;
2-[4-(2S-hexyloxy)-2-fluorophenyl]-5-propylpyridine;
2-[4-(2S-hexyloxy)-2-fluorophenyl]-5-butylpyridine;
2-[4-(2S-hexyloxy)-2-fluorophenyl]-5-pentylpyridine;
2-[4-(2S-hexyloxy)-2-fluorophenyl]-5-hexylpyridine;
2-[4-(2S-hexyloxy)-2-fluorophenyl]-5-heptylpyridine;
2-[4-(2S-hexyloxy)-2-fluorophenyl]-5-octylpyridine;
2-[4-(2S-hexyloxy)-2-fluorophenyl]-5-nonylpyridine;
2-[4-(2S-hexyloxy)-2-fluorophenyl]-5-decylpyridine;
2-(4-heptyloxy-2-fluorophenyl)-5-propylpyridine;
2-(4-heptyloxy-2-fluorophenyl)-5-butylpyridine;
2-(4-heptyloxy-2-fluorophenyl)-5-pentylpyridine;
2-(4-heptyloxy-2-fluorophenyl)-5-hexylpyridine;
2-(4-heptyloxy-2-fluorophenyl)-5-heptylpyridine;
2-(4-heptyloxy-2-fluorophenyl)-5-octylpyridine;
2-(4-heptyloxy-2-fluorophenyl)-5-nonylpyridine;
2-(4-heptyloxy-2-fluorophenyl)-5-decylpyridine;

2-(4-octyloxy-2-fluorophenyl)-5-propylpyridine;
2-(4-octyloxy-2-fluorophenyl)-5-butylpyridine;
2-(4-octyloxy-2-fluorophenyl)-5-pentylpyridine;
2-(4-octyloxy-2-fluorophenyl)-5-hexylpyridine;
2-(4-octyloxy-2-fluorophenyl)-5-heptylpyridine;
2-(4-octyloxy-2-fluorophenyl)-5-octylpyridine;
2-(4-octyloxy-2-fluorophenyl)-5-nonylpyridine;
2-(4-octyloxy-2-fluorophenyl)-5-decylpyridine;
2-[4-(2S-octyloxy)-2-fluorophenyl]-5-pentylpyridine;
2-[4-(2S-octyloxy)-2-fluorophenyl]-5-hexylpyridine;
2-[4-(2S-octyloxy)-2-fluorophenyl]-5-heptylpyridine;
2-[4-(2S-octyloxy)-2-fluorophenyl]-5-octylpyridine;
2-[4-(2S-octyloxy)-2-fluorophenyl]-5-nonylpyridine;
2-[4-(2S-octyloxy)-2-fluorophenyl]-5-decylpyridine;
2-(4-nonyloxy-2-fluorophenyl)-5-octylpyridine;
2-(4-nonyloxy-2-fluorophenyl)-5-nonylpyridine;
2-(4-nonyloxy-2-fluorophenyl)-5-decylpyridine;
2-(4-decyloxy-2-fluorophenyl)-5-heptylpyridine;
2-(4-decyloxy-2-fluorophenyl)-5-octylpyridine;
2-(4-decyloxy-2-fluorophenyl)-5-nonylpyridine;
2-(4-methyl-2-fluorophenyl)-5-methylpyridine;
2-(4-methyl-2-fluorophenyl)-5-ethylpyridine;
2-(4-methyl-2-fluorophenyl)-5-propylpyridine;
2-(4-methyl-2-fluorophenyl)-5-butylpyridine;
2-(4-methyl-2-fluorophenyl)-5-pentylpyridine;
2-(4-methyl-2-fluorophenyl)-5-hexylpyridine;
2-(4-methyl-2-fluorophenyl)-5-heptylpyridine;
2-(4-ethyl-2-fluorophenyl)-5-methylpyridine;
2-(4-ethyl-2-fluorophenyl)-5-ethylpyridine;
2-(4-ethyl-2-fluorophenyl)-5-propylpyridine;
2-(4-ethyl-2-fluorophenyl)-5-butylpyridine;
2-(4-ethyl-2-fluorophenyl)-5-pentylpyridine;
2-(4-propyl-2-fluorophenyl)-5-methylpyridine;
2-(4-propyl-2-fluorophenyl)-5-ethylpyridine;
2-(4-propyl-2-fluorophenyl)-5-propylpyridine;
2-(4-propyl-2-fluorophenyl)-5-butylpyridine;
2-(4-propyl-2-fluorophenyl)-5-pentylpyridine;
2-(4-butyl-2-fluorophenyl)-5-methylpyridine;
2-(4-butyl-2-fluorophenyl)-5-ethylpyridine;
2-(4-butyl-2-fluorophenyl)-5-propylpyridine;
2-(4-pentyl-2-fluorophenyl)-5-methylpyridine:
2-(4-pentyl-2-fluorophenyl)-5-ethylpyridine;
2-(4-pentyl-2-fluorophenyl)-5-propylpyridine;
2-(4-hexyl-2-fluorophenyl)-5-methylpyridine;
2-(4-hexyl-2-fluorophenyl)-5-ethylpyridine;
2-(4-hexyl-2-fluorophenyl)-5-propylpyridine;
2-(4-heptyl-2-fluorophenyl)-5-methylpyridine;
2-(4-heptyl-2-fluorophenyl)-5-ethylpyridine;
2-(4-methoxy-2-fluorophenyl)-5-(trans-4-methylcyclohexyl)pyridine;
2-(4-methoxy-2-fluorophenyl)-5-(trans-4-ethylcyclohexyl)pyridine, m.p. (C-N) 55.0° C., cl.p. (N-I) 155.0° C.;
2-(4-methoxy-2-fluorophenyl)-5-(trans-4-butylcyclohexyl)pyridine;
2-(4-methoxy-2-fluorophenyl)-5-(trans-4-pentylcyclohexyl)pyridine, m.p. (C-N) 44.6° C., cl.p. (N-I) 177.6° C., Δε (56° C.)=0.4, ε (56° C.)=3.68;
2-(4-methoxy-2-fluorophenyl)-5-(trans-4-hexylcyclohexyl)pyridine;
2-(4-methoxy-2-fluorophenyl)-5-(trans-4-heptylcyclohexyl)pyridine;
2-(4-ethoxy-2-fluorophenyl)-5-(trans-4-methylcyclohexyl)pyridine;
2-(4-ethoxy-2-fluorophenyl)-5-(trans-4-ethylcyclohexyl)pyridine;
2-(4-ethoxy-2-fluorophenyl)-5-(trans-4-propylcyclohexyl)pyridine; 2-(4-ethoxy-2-fluorophenyl)-5-(trans-4-butylcyclohexyl)pyridine;
2-(4-ethoxy-2-fluorophenyl)-5-(trans-4-pentylcyclohexyl)pyridine;
2-(4-propyloxy-2-fluorophenyl)-5-(trans-4-methylcyclohexyl)pyridine;
2-(4-propyloxy-2-fluorophenyl)-5-(trans-4-ethylcyclohexyl)pyridine; 0 2-(4-propyloxy-2-fluorophenyl)-5-(trans-4-propylcyclohexyl)pyridine;
2-(4-butyloxy-2-fluorophenyl)-5-(trans-4-methylcyclohexyl)pyridine;
2-(4-butyloxy-2-fluorophenyl)-5-(trans-4-ethylcyclohexyl)pyridine;
2-(4-butyloxy-2-fluorophenyl)-5-(trans-4-propylcyclohexyl)pyridine;
2-(4-pentyloxy-2-fluorophenyl)-5-(trans-4-methylcyclohexyl)pyridine;
2-(4-pentyloxy-2-fluorophenyl)-5-(trans-4-ethylcyclohexyl)pyridine;
2-(4-pentyloxy-2-fluorophenyl)-5-(trans-4-propylcyclohexyl)pyridine;
2-(4-hexyloxy-2-fluorophenyl)-5-(trans-4-octylcyclohexyl)pyridine;
2-(4-hexyloxy-2-fluorophenyl)-5-(trans-4-nonylcyclohexyl)pyridine;
2-(4-hexyloxy-2-fluorophenyl)-5-(trans-4-decylcyclohexyl)pyridine;
2-[4-(2S-hexyloxy)-2-fluorophenyl]-5-(trans-4-octylcyclohexyl)pyridine; 0 2-[4-(2S-hexyloxy)-2-fluorophenyl]-5-(trans-4-nonylcyclohexyl)pyridine;
2-[4-(2S-hexyloxy)-2-fluorophenyl]-5-(trans-4-decylcyclohexyl)pyridine;
2-(4-heptyloxy-2-fluorophenyl)-5-(trans-4-heptylcyclohexyl)pyridine;
2-(4-heptyloxy-2-fluorophenyl)-5-(trans-4-octylcyclohexyl)pyridine;
2-(4-heptyloxy-2-fluorophenyl)-5-(trans-4-nonylcyclohexyl)pyridine;
2-(4-heptyloxy-2-fluorophenyl)-5-(trans-4-decylcyclohexyl)pyridine;
2-(4-octyloxy-2-fluorophenyl)-5-(trans-4-hexylcyclohexyl)pyridine;
2-(4-octyloxy-2-fluorophenyl)-5-(trans-4-heptylcyclohexyl)pyridine;
2-(4-octyloxy-2-fluorophenyl)-5-(trans-4-octylcyclohexyl)pyridine;
2-(4-octyloxy-2-fluorophenyl)-5-(trans-4-nonylcyclohexyl)pyridine;
2-(4-octyloxy-2-fluorophenyl)-5-(trans-4-decylcyclohexyl)pyridine;
2-[4-(2S-octyloxy)-2-fluorophenyl]-5-(trans-4-hexylcyclohexyl)pyridine;
2-[4-(2S-octyloxy)-2-fluorophenyl]-5-(trans-4-heptylcyclohexyl)pyridine;
2-[4-(2S-octyloxy)-2-fluorophenyl]-5-(trans-4-octylcyclohexyl)pyridine;
2-[4-(2S-octyloxy)-2-fluorophenyl]-5-(trans-4-nonylcyclohexyl)pyridine;
2-[4-(2S-octyloxy)-2-fluorophenyl]-5-(trans-4-decylcyclohexyl)pyridine;
2-(4-nonyloxy-2-fluorophenyl)-5-(trans-4-hexylcyclohexyl)pyridine;
2-(4-nonyloxy-2-fluorophenyl)-5-(trans-4-heptylcyclohexyl)pyridine;
2-(4-nonyloxy-2-fluorophenyl)-5-(trans-4-octylcyclohexyl)pyridine;

2-(4-methyl-2-fluorophenyl)-5-(trans-4-methylcyclohexyl)pyridine;
2-(4-methyl-2-fluorophenyl)-5-(trans-4-ethylcyclohexyl)pyridine;
2-(4-methyl-2-fluorophenyl)-5-(trans-4-propylcyclohexyl)pyridine;
2-(4-methyl-2-fluorophenyl)-5-(trans-4-butylcyclohexyl)pyridine;
2-(4-methyl-2-fluorophenyl)-5-(trans-4-pentylcyclohexyl)pyridine;
2-(4-ethyl-2-fluorophenyl)-5-(trans-4-methylcyclohexyl)pyridine;
2-(4-ethyl-2-fluorophenyl)-5-(trans-4-ethylcyclohexyl)pyridine;
2-(4-ethyl-2-fluorophenyl)-5-(trans-4-propylcyclohexyl)pyridine;
2-(4-ethyl-2-fluorophenyl)-5-(trans-4-butylcyclohexyl)pyridine;
2-(4-ethyl-2-fluorophenyl)-5-(trans-4-pentylcyclohexyl)pyridine;
2-(4-propyl-2-fluorophenyl)-5-(trans-4-methylcyclohexyl)pyridine;
2-(4-propyl-2-fluorophenyl)-5-(trans-4-ethylcyclohexyl)pyridine;
2-(4-propyl-2-fluorophenyl)-5-(trans-4-propylcyclohexyl)pyridine;
2-(4-propyl-2-fluorophenyl)-5-(trans-4-butylcyclohexyl)pyridine;
2-(4-propyl-2-fluorophenyl)-5-(trans-4-pentylcyclohexyl)pyridine;
2-(4-butyl-2-fluorophenyl)-5-(trans-4-methylcyclohexyl)pyridine;
2-(4-butyl-2-fluorophenyl)-5-(trans-4-ethylcyclohexyl)pyridine;
2-(4-butyl-2-fluorophenyl)-5-(trans-4-propylcyclohexyl)pyridine;
2-(4-pentyl-2-fluorophenyl)-5-(trans-4-methylcyclohexyl)pyridine;
2-(4-pentyl-2-fluorophenyl)-5-(trans-4-ethylcyclohexyl)pyridine;
2-(4-pentyl-2-fluorophenyl)-5-(trans-4-propylcyclohexyl)pyridine;
2-[4-(trans-4-methylcyclohexyl)-2-fluorophenyl]-5-methylpyridine;
2-[4-(trans-4-methylcyclohexyl)-2-fluorophenyl]-5-ethylpyridine;
2-[4-(trans-4-methylcyclohexyl)-2-fluorophenyl]-5-propylpyridine;
2-[4-(trans-4-methylcyclohexyl)-2-fluorophenyl]-5-butylpyridine;
2-[4-(trans-4-methylcyclohexyl)-2-fluorophenyl]-5-pentylpyridine;
2-[4-(trans-4-ethylcyclohexyl)-2-fluorophenyl]-5-methylpyridine;
2-[4-(trans-4-ethylcyclohexyl)-2-fluorophenyl]-5-ethylpyridine;
2-[4-(trans-4-ethylcyclohexyl)-2-fluorophenyl]-5-propylpyridine;
2-[4-(trans-4-ethylcyclohexyl)-2-fluorophenyl]-5-butylpyridine;
2-[4-(trans-4-ethylcyclohexyl)-2-fluorophenyl]-5-pentylpyridine;
2-[4-(trans-4-propylcyclohexyl)-2-fluorophenyl]-5-methylpyridine;
2-[4-(trans-4-propylcyclohexyl)-2-fluorophenyl]-5-etbylpyridine:
2-[4-(trans-4-propylcyclohexyl)-2-fluorophenyl]-5-propylpyridine;
2-[4-(trans-4-propylcyclohexyl)-2-fluorophenyl]-5-butylpyridine;
2-[4-(trans-4-propylcyclohexyl)-2-fluorophenyl]-5-pentylpyridine;
2-[4-(trans-4-butylcyclohexyl)-2-fluorophenyl]-5-methylpyridine;
2-[4-(trans-4-butylcyclohexyl)-2-fluorophenyl]-5-ethylpyridine;
2-[4-(trans-4-butylcyclohexyl)-2-fluorophenyl]-5-propylpyridine;
2-[4-(trans-4-pentylcyclohexyl)-2-fluorophenyl]-5-methylpyridine;
2-[4-(trans-4-pentylcyclohexyl)-2-fluorophenyl]-5-ethylpyridine;
2-[4-(trans-4-pentylcyclohexyl)-2-fluorophenyl]-5-propylpyridine;
2-[4-(trans-4-methylcyclohexyl)-2-fluorophenyl]-5-(trans-4-methylcyclohexyl)pyridine;
2-[4-(trans-4-methylcyclohexyl)-2-fluorophenyl]-5-(trans-4-ethylcyclohexyl)pyridine;
2-[4-(trans-4-methylcyclohexyl)-2-fluorophenyl]-5-(trans-4-propylcyclohexyl)pyridine;
2-[4-(trans-4-methylcyclohexyl)-2-fluorophenyl]-5-(trans-4-butylcyclohexyl)pyridine;
2-[4-(trans-4-methylcyclohexyl)-2-fluorophenyl]-5-(trans-4-pentylcyclohexyl)pyridine;
2-[4-(trans-4-ethylcyclohexyl)-2-fluorophenyl]-5-(trans-4-methylcyclohexyl)pyridine;
2-[4-(trans-4-ethylcyclohexyl)-2-fluorophenyl]-5-(trans-4-ethylcyclohexyl)pyridine;
2-[4-(trans-4-ethylcyclohexyl)-2-fluorophenyl]-5-(trans-4-propylcyclohexyl)pyridine;
2-[4-(trans-4-ethylcyclohexyl)-2-fluorophenyl]-5-(trans-4-butylcyclohexyl)pyridine;
2-[4-(trans-4-ethylcyclohexyl)-2-fluorophenyl]-5-(trans-4-pentylcyclohexyl)pyridine;
2-[4-(trans-4-propylcyclohexyl)-2-fluorophenyl]-5-(trans-4-methylcyclohexyl)pyridine;
2-[4-(trans-4-propylcyclohexyl)-2-fluorophenyl]-5-(trans-4-ethylcyclohexyl)pyridine:
2-[4-(trans-4-propylcyclohexyl)-2-fluorophenyl]-5-(trans-4-propylcyclohexyl)pyridine;
2-[4-(trans-4-propylcyclohexyl)-2-fluorophenyl]-5-(trans-4-butylcyclohexyl)pyridine;
2-[4-(trans-4-propylcyclohexyl)-2-fluorophenyl]-5-(trans-4-pentylcyclohexyl)pyridine;
2-[4-(trans-4-butylcyclohexyl)-2-fluorophenyl]-5-(trans-4-methylcyclohexyl)pyridine;
2-[4-(trans-4-butylcyclohexyl)-2-fluorophenyl]-5-(trans-4-ethylcyclohexyl)pyridine;
2-[4-(trans-4-butylcyclohexyl)-2-fluorophenyl]-5-(trans-4-propylcyclohexyl)pyridine;
2-[4-(trans-4-pentylcyclohexyl)-2-fluorophenyl]-5-(trans-4-methylcyclohexyl)pyridine;
2-[4-(trans-4-pentylcyclohexyl)-2-fluorophenyl]-5-(trans-4-ethylcyclohexyl)pyridine;
2-[4-(trans-4-pentylcyclohexyl)-2-fluorophenyl]-5-(trans-4-propylcyclohexyl)pyridine.

EXAMPLE 4

In order to illustrate the mixtures in accordance with the invention, the following mixture was prepared and its electro-optical data were measured at room temperature in a TN cell:

MIXTURE A 19 wt. % of 5-propyl-2-(4-cyanophenyl)pyridine,
29 " 5-pentyl-2-(4-cyanophenyl)pyridine, 26 " trans-4-butylcyclohexanecarboxylic acid 4-ethoxyphenyl ester, 16 " trans-4-hexylcyclohexanecarboxylic acid 4-ethoxyphenyl ester, 10 " 2-(4-methoxy-2-fluorophenyl)-5-(trans-4-pentylcyclohexyl)pyridine;

phase transition (S-N) $< -20°$ C., cl.p. (N-I) 63.5° C.;

$\Delta\epsilon = 11.5$, $V_{10} = 1.52$ V. $\Delta n = 0.162$.

We claim:

1. A compound represented by the formula

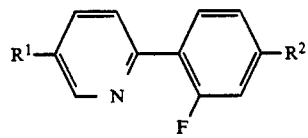

I wherein $R^1$ is $C_1$-$C_{12}$-alkyl or trans-4-($C_1$-$C_{18}$-alkyl)-cyclohexyl; and $R^2$ is $C_1$-$C_{12}$-alkyl or $C_1$-$C_{12}$-alkoxy.

2. A compound according to claim 1, wherein $R^1$ is $C_1$-$C_{12}$-alkyl or trans-4-($C_1$-$C_{12}$-alkyl)-cyclohexyl.

3. A compound according to claim 2, wherein $R^1$ is $C_1$-$C_7$-alkyl or trans-4-($C_1$-$C_7$-alkyl)cyclohexyl.

4. A compound according to claim 1, wherein $R^2$ is $C_1$-$C_7$-alkyl or $C_1$-$C_7$-alkoxy.

5. A compound according to claim 1, wherein $R^2$ is a $C_1$-$C_{12}$-alkoxy group.

* * * * *